(12) United States Patent
Dexheimer

(10) Patent No.: US 6,919,486 B2
(45) Date of Patent: Jul. 19, 2005

(54) POLYETHEROLS PRODUCED USING ALUMINIUM PHOSPHONATE CATALYSTS

(75) Inventor: Edward M. Dexheimer, Grosse Ile, MI (US)

(73) Assignee: BASF Corporation, Florham Park, NJ (US)

( * ) Notice: Subject to any disclaimer, the term of this patent is extended or adjusted under 35 U.S.C. 154(b) by 0 days.

(21) Appl. No.: 10/036,679

(22) Filed: Dec. 21, 2001

(65) Prior Publication Data

US 2003/0135074 A1 Jul. 17, 2003

(51) Int. Cl.$^7$ ............................................. C07C 43/11
(52) U.S. Cl. ...................... 568/620; 568/619; 568/623; 568/624; 568/679; 568/680; 528/425; 528/485; 525/88
(58) Field of Search ................. 568/620, 619, 568/623, 624, 679, 680; 528/425, 485; 525/88; 252/182.12, 182.35

(56) References Cited

U.S. PATENT DOCUMENTS

| | | | |
|---|---|---|---|
| 3,657,149 A | 4/1972 | Vandenberg et al. ......... 502/154 |
| 3,657,159 A | 4/1972 | Vandenberg et al. ......... 528/409 |
| 3,697,496 A | 10/1972 | Ueno et al. .................. 526/186 |
| 4,209,609 A | 6/1980 | Haas | |
| 4,304,729 A | 12/1981 | Greco et al. .................. 556/13 |
| 4,554,295 A | 11/1985 | Ridge, Jr. | |
| 4,721,817 A | * 1/1988 | Edwards ...................... 568/618 |
| 4,810,729 A | 3/1989 | Davis et al. | |
| 5,637,673 A | 6/1997 | Le-Khac | |
| 5,830,926 A | 11/1998 | Smiecinski et al. | |
| 5,919,988 A | 7/1999 | Pazos et al. ................. 568/679 |
| 6,100,363 A | 8/2000 | Sampara et al. | |
| 6,103,850 A | * 8/2000 | Reichel et al. ................ 528/60 |
| 6,165,399 A | 12/2000 | Guntherberg et al. | |
| 6,197,839 B1 | 3/2001 | Genz et al. | |
| 6,228,899 B1 | 5/2001 | Wetterling et al. | |
| 6,284,812 B1 | 9/2001 | Rotermund et al. | |
| 6,310,114 B1 | 10/2001 | Genz et al. | |
| 6,319,985 B1 | 11/2001 | Bruning et al. | |
| 6,383,970 B1 | 5/2002 | Mimura et al. ............. 502/162 |
| 6,492,565 B2 | 12/2002 | Denninger et al. | |

FOREIGN PATENT DOCUMENTS

| | | |
|---|---|---|
| DE | 1937728 | 2/1970 |
| DE | 10030413 | 3/2001 |
| EP | 273521 | 12/1987 |
| EP | 761708 | 8/1996 |
| EP | 992524 | 9/1999 |
| JP | 7130705 | 9/1971 |

OTHER PUBLICATIONS

PCT Search Report dated Oct. 21, 2002.
Chemical Abstracts, vol. 76, No. 10, Mar. 6, 1972, Ueno et al.: "Polymerisation Catalysts for Alkylene Oxides" XP002217502 Abstract & JP 07 130405 A (Sumitomo Chemical Co. Ltd.).
Hong–Quan; Ring–Opening Polymerization of Epichlorohydrin and its Copolymerization With Other Alkylene Oxides by Quaternary Catalyst System; Department of Chemistry, Huazhong University of Science and Technology; May 20, 2000; P–2446–2454; Wuhan.
Mark R. Mason; Alisa M. Perkins; Journal of Organometallic Chemistry 599 (2000) 200–207; Toledo, Ohio.
EPO Search Report; PCT/EP02/06693;PCT/IPEA/408.

* cited by examiner

*Primary Examiner*—Rosalynd Keys
(74) *Attorney, Agent, or Firm*—Fernando A. Borrego; Howard & Howard Attys

(57) ABSTRACT

A method for the production of polyetherols using aluminum phosphonate catalysts is disclosed. Reaction products of the process include various polyetherols including very low unsaturation polyether polyols. The aluminum phosphonate catalyst preferably has a general structure of RPO-(OAlR'R'')$_2$, wherein O represents oxygen, P represents pentavalent phosphorous, Al represents aluminum, R comprises a hydrogen, an alkyl group, or an aryl group, and R' and R'' independently comprise a halide, an alkyl group, an alkoxy group, an aryl group, or an aryloxy group. Polyols produced according to the disclosed procedure have properties very similar to or more beneficial than those produced utilizing the typical base catalysts.

59 Claims, No Drawings

POLYETHEROLS PRODUCED USING ALUMINIUM PHOSPHONATE CATALYSTS

BACKGROUND OF THE INVENTION

This invention relates generally to polyether polyols formed using aluminum phosphonate catalysts and, more particularly, to formation of polyetherols having very low unsaturation using aluminum phosphonate catalysts.

Polyoxyalkylene polyether polyols are well known compounds utilized in the formation of a variety of polyurethane products, such as foams, coatings, adhesives, sealants and elastomers. As a general matter, these polyols are produced by polyoxyalkylation of an initiator molecule with ethylene oxide, propylene oxide, butylene oxides, or mixtures thereof. The initiator molecules contain alkylene oxide-reactive hydrogens like hydroxyls and amines. This oxyalkylation is generally conducted in the presence of a catalyst. The most common catalysts are basic metal catalysts such as sodium hydroxide, potassium hydroxide, or alkali metal alkoxides. One advantage of these base catalysts is that they are inexpensive and readily available. Use of these base catalysts, however, is associated with a range of problems. One of the major problems is that the oxyalkylation with propylene oxide has associated with it a competing rearrangement of the propylene oxide into allyl alcohol, which continually introduces a monohydroxyl-functional molecule. This monohydroxyl-functional molecule is also capable of being oxyalkylated. In addition, it can act as a chain terminator during the reaction with isocyanates to produce the final urethane product. Thus, as the oxyalkylation reaction is continued more of this product, generally measured as the unsaturation content of the polyol, is formed. This leads to reduced functionality of the polyol and a broadening of the molecular weight distribution of the final polyol mixture. The amount of unsaturation content may approach 30 to 40% with unsaturation levels of 0.08 meq/g KOH or higher.

In an attempt to reduce the unsaturation content of polyols a number of other catalysts have been developed. One such group of catalysts includes the hydroxides formed from rubidium, cesium, barium, and strontium. These catalysts also present a number of problems. The catalysts only slightly reduce the degree of unsaturation, are much more expensive, and some of them are toxic. Like potassium hydroxide catalysts, these higher molecular weight hydroxide catalysts are known to affect the polyurethane forming reaction, they are generally removed prior to work-up of any polyol for use in polyurethane systems.

A second line of alternative catalyst development has been formation of double metal cyanide (DMC) catalysts. These catalysts are typically based on zinc hexacyanocobaltate. With the use of DMC catalysts it is possible to achieve unsaturations in the range of 0.003 to 0.010 meq/g KOH. While the DMC catalysts would seem to be highly beneficial they also are associated with a number of difficulties. As a first difficulty there is a relatively high capital cost involved in scaling up of and utilization of DMC catalysts. The catalysts themselves have an extremely high cost compared to the base catalysts. The process of making polyols using DMC is also different from based catalyzed reactions. During use of DMC catalysts there is an initial significant, and often unpredictable, lag time before the catalyst begins catalyzing the reaction. Another difficulty is that ethylene oxide does not add uniformly to growing polymer chains utilizing DMC catalysts. Chain transfer is slow relative to chain growth, so all the ethylene oxide adds to only a few of the polymer chains, leaving the rest unreacted. The result is a polyol of such low quality that it has no commercial value. To add ethylene oxide to a growing chain the DMC catalysts must be replaced with the typical base catalysts, thus adding steps. In addition, it is generally believed that the DMC catalysts should be removed prior to work-up of any polyol for use in polyurethane systems. Finally, polyols generated using DMC catalysts are not mere "drop in" replacements for similar size and functionality polyols produced using the typical base catalysts. Indeed, it has been found that often DMC catalyzed polyols have properties very different from equivalent polyols produced using, for example, potassium hydroxide. It is recognized in the art that polyols made utilizing DMC catalysts contain small amounts of high molecular weight compounds which can affect utilization of these polyols in polyurethane systems, particularly foaming. The so-called high molecular weight tail has been identified in amounts of greater than 100 ppm and variously described as polymer of molecular weight greater than 50,000 Daltons, see U.S. Pat. No. 5,919,988 which is incorporated herein by reference. The presence of the so-called high molecular weight tail in amounts of greater than 300 has been identified as a cause of foam destabilization and collapse.

Thus, there exists a need for a class of catalysts that can be used for the oxyalkylation of initiator molecules by alkylene oxides that is inexpensive, capable of producing very low unsaturation polyols, does not require removal from the polyol prior to utilization in polyurethane systems, and that produces a polyol having properties that are the same or better than those in a polyol produced using base catalysts. Preferably the new class of catalysts can be used in existing systems and equipment using standard manufacturing conditions.

SUMMARY OF THE INVENTION

In general terms, the present invention provides low unsaturation polyetherols produced using an aluminum phosphonate catalyst and provides for their use in polyurethane applications.

In one embodiment, the present invention is low unsaturation polyether polyols produced according to a process comprising the steps of: providing at least one alkylene oxide; providing at least one initiator molecule having at least one alkylene oxide reactive hydrogen; and reacting the at least one alkylene oxide with the at least one initiator molecule in the presence of an aluminum phosphonate catalyst to form a polyether polyol.

In another embodiment, the present invention is low unsaturation polyether polyols produced according to a process comprising the steps of: providing at least one alkylene oxide; providing at least one initiator molecule having at least one alkylene oxide reactive hydrogen; providing an aluminum phosphonate catalyst having the general structure of RPO-(OAlR'R")2, wherein O represents oxygen, P represents pentavalent phosphorous, Al represents aluminum, R comprises a hydrogen, a methyl group, an alkyl group, or an aryl group, and R' and R" independently comprise a halide, an alkyl group, an alkoxy group, an aryl group, or an aryloxy group; and then reacting the at least one alkylene oxide with the at least one initiator molecule in the presence of the aluminum phosphonate catalyst to form a polyether polyol.

Another embodiment comprises a polyether polyol prepared in the presence of an aluminum phosphonate catalyst, wherein an oligomer comprising the reaction product of a pre-reaction initiator molecule with at least one alkylene oxide is one of the at least one initiator molecules. In a further embodiment the oligomer has a number average molecular weight of from 200 to 1500 Daltons.

Another embodiment comprises a polyether polyol containing an aluminum phosphonate. The aluminum phosphonate is present at levels of from approximately 0.01 to 5.0 weight percent based on the total weight of the polyether polyol. In a further embodiment, the polyether polyol contains an aluminum phosphonate catalyst having the general structure of RPO-(OAlR'R")2 wherein P represents pentavalent phosphorous; R comprises a hydrogen, an alkyl group, or an aryl group; and R' and R" independently comprise a halide, an alkyl group, an alkoxy group, an aryl group, or an aryloxy group. In a yet further embodiment, R is a methyl group; and R' and R" independently comprise one of an ethyl group, an ethoxy group, a propyl group, a propoxy group, a butyl group, a butoxy group, a phenyl group, or a phenoxy group.

In another embodiment, the present invention low unsaturation polyether polyols produced as the reaction product of propylene oxide and at least one initiator molecule having at least one propylene oxide reactive hydrogen reacted in the absence of DMC catalyst, wherein said polyol consists essentially of molecules having an equivalent weight of 1000 to 2000 Daltons and an unsaturation of less than or equal to 0.020 meq/g KOH.

In yet another embodiment the present invention is a polyurethane foam produced according to a process comprising the steps of: providing at least one alkylene oxide; providing at least one initiator molecule having at least one alkylene oxide reactive hydrogen; reacting the at least one alkylene oxide with the at least one initiator molecule in the presence of an aluminum phosphonate catalyst to form a polyether polyol; and reacting the polyether polyol formed in step c) with at least one polyisocyanate in the presence of a blowing agent to form a polyurethane foam.

These and other features and advantages of this invention will become more apparent to those skilled in the art from the detailed description of a preferred embodiment.

DETAILED DESCRIPTION OF A PREFERRED EMBODIMENT

The present invention discloses use of aluminum phosphonate catalysts to catalyze the oxyalkylation of initiator molecules. Use of this catalyst enables production of polyols having very low unsaturation compared to a similar size polyol produced using typical base catalysts. In addition, other than the very low degree of unsaturation, these polyols have properties that are the same or better than those produced using the typical base catalysts. The aluminum phosphonate catalysts can be synthesized in a very straight-forward manner and are inexpensive compared to the other catalysts capable of producing these very low unsaturation polyols. We have also found that aluminum phosphonate catalysts did not have to be removed after formation of the polyol prior to its utilization in polyurethane systems. The aluminum phosphonate catalysts can be readily substituted in existing polyurethane oxyalkylation procedures that utilize base catalysts such as potassium hydroxide with substantially no modifications to the procedure. Unlike the DMC class of catalysts these aluminum phosphonate catalysts exhibit no lag time and are capable of polyoxyalkylation utilizing ethylene oxide.

Synthesis of the Aluminum Phosphonate Catalysts

The aluminum phosphonate catalysts of the present invention can be produced by a number of processes, one of which is described in detail below. In general the procedure involves reacting a pentavalent phosphonic acid with a tri-substituted aluminum compound to produce an aluminum phosphonate. The pentavalent phosphonic acids that are suitable have the general structure of $RPO(OH)_2$, wherein: R represents a hydrogen group, and alkyl group, or an aryl group; P represents a pentavalent phosphorous; O represents oxygen; and H represents hydrogen. Some examples include phosphonic acid, methylphosphonic acid, ethylphosphonic acid, propylphosphonic acid, i- t- or sec-butylphosphonic acids, and phenylphosphonic acid. The tri-substituted aluminum compounds have the general structure of $AlR'_3$, wherein R' is a methyl group, an alkyl group, an alkoxy group, an aryl group, or an aryloxy group. Some examples include trimethylaluminum, triethylaluminum, triethoxyaluminum, tri-n-propylaluminum, tri-n-propoxyaluminum, tri-iso-butylaluminum, tri-sec-butylaluminum, tri-tert-butylaluminum, tri-iso-butoxyaluminum, tri-sec-butoxyaluminum, tri-tert-butoxyaluminum, triphenylaluminum, and triphenoxyaluminum.

An aluminum phosphonate catalyst according to the present invention, bis(diisobutylaluminum) methylphosphonate, is synthesized as follows. A solution of 6.25 g of methylphosphonic acid in 125 ml of dry tetrahydrofuran is dissolved in a 250 ml erlenmeyer flask at approximately 25° C. with magnetic stirring. Using a glass syringe, 100 ml of triisobutylaluminum, 25% weight solution in toluene, is transferred into a 500 ml 3-neck round bottomed flask swept with nitrogen. The flask also includes a thermometer, magnetic stir bar and a 250 ml addition funnel. The triisobutylaluminum solution is cooled to 0° C. using a sodium chloride and ice water bath. The flask is swept with nitrogen throughout the setup procedure. The methylphosphonic acid solution is added to the addition funnel and then is added dropwise to the triisobutylaluminum solution under a nitrogen blanket at 0° C. The resulting solution is a clear, colorless, homogeneous solution and there is very little exothermic reaction. After all of the methylphosphonic acid has been added the reaction mixture is slowly warmed to approximately 25° C. and held there for 1 hour with stirring. After 1 hour the stirring is stopped and the mixture is maintained under a nitrogen blanket for approximately 12 hours. Then the nitrogen is stopped and the volatiles are removed by vacuum stripping for 3 hours at 25° C. After the vacuum stripping is completed the vacuum is relieved and 75 g of toluene is added. The toluene solution is stirred for 1 hour and the resulting clear, colorless, homogeneous solution is used as detailed below. This synthetic pathway is similar to that reported in the article by Mark R. Mason et al. entitled "Alkylaluminophosphonate-catalyzed ring-opening homopolymerization of epichlorohydrin and propylene oxide", Journal of Organometallic Chemistry 2000, 599, 200–207, herein incorporated by reference.

The formation of polyols for use in polyurethane systems utilizing a polyoxyalkylation of an initiator molecule by alkylene oxides is well known in the art. The present aluminum phosphonate catalysts can be used as replacements for base catalysts in substantially all processes used for the base catalysts with few, if any, changes to the procedure. As non-limiting examples, aluminum phosphonate catalysts can be used to make homogeneous polyoxyalkylation products, i.e. homopolymers; heterogeneous polyoxyalkylation products, i.e. heteric polyether polyols, various copolymers, including polymers having sections of different composition, e.g. block copolymers.

Unlike base catalysts, the present aluminum phosphonate catalysts are water sensitive. Preferably water levels of all components used in polyol formation reactions are at or below 0.1 weight percent of the particular component, most preferably at or below 0.05 weight percent. It will be understood that any minor changes required for optimization of a process using an aluminum phosphonate catalyst, e.g. adjusting water levels or amounts of components, would be well within the ability of one of ordinary skill in the art and would not require extensive experimentation.

Initiator molecules suitable for the present invention include all initiators having at least one alkylene oxide reactive hydrogen such as alcohols, polyhydric alcohols and amine compounds. Examples of alcohols include aliphatic and aromatic alcohols, such as lauryl alcohol, nonylphenol, octylphenol and C12 to C18 fatty alcohols. Examples of the polyhydric alcohols include diols, triols, and higher functional alcohols such as sucrose, and sorbitol. Amine compounds include the diamines such as ethylene diamine, toluene diamine, and other polyamines. In a preferred embodiment these initiator compounds are utilized to form oligomers having number average molecular weights of from about 200 to 1500. These oligomers can be formed utilizing known methods, e.g. self-catalyzing initiators or base catalysts, to add a plurality of alkylene oxides to the initiator molecules in a pre-reaction step. The oligomer molecules can then be utilized with the aluminum phosphonate catalysts of the present invention.

The aluminum phosphonate catalysts of the present invention can also be used to modify polyols of a variety of sizes. This modification can take the form of capping an existing polyol with ethylene oxide, propylene oxide, butylene oxide, epichlorohydrin, or mixtures of these and other alkylene oxides. The polyols can be prepared using any of the known catalysts and may range in size from a number average molecular weight of 200 to 10,000 Daltons. An example of this modification process is described below in example 5. As used in the present specification and claims, the term initiator molecule is intended to encompass the short typical initiator molecules, oligomers and polyols to be modified as described in this specification.

Specific examples of the utilization of the aluminum phosphonate catalysts of the present invention are described in detail below. The general procedure comprises reacting the initiator molecule with at least one alkylene oxide or a mixture of alkylene oxides in the presence of the aluminum phosphonate catalysts. Typical alkylene oxides include ethylene oxide, propylene oxide, butylene oxide, and epichlorohydrin. The initiator molecule and the alkylene oxide or oxides are reacted for periods of from 15 minutes to 15 hours. The reaction is generally conducted at a temperature of from 95° C. to 150° C., and most preferably at a temperature between 105° C. to 130° C. Oxyalkylation reactions conducted according to the present invention will result in the formation of polyols having unsaturation levels of less than 0.015 meq/g KOH. Most preferably, the procedure is utilized to produce polyols having unsaturation levels of less than 0.010 meg/g KOH.

Generally, the aluminum phosphonate catalysts are utilized at levels of from 0.1 to 5.0 weight percent based on the total weight of the final product, most preferably at levels of from 0.1 to 0.5 weight percent. One notable difference between the aluminum phosphonate catalysts of the present invention and the DMC catalysts is that the aluminum phosphonate catalysts do not exhibit any reaction lag time during the oxyalkylation reaction. Another difference is the absence of formation of the so-called high molecular weight tail found in polyols produced using DMC catalysts. Once formed, polyols of the present invention can be utilized in any of the polyurethane procedures including formation of foams, coatings, adhesives, sealants, elastomers, and polymer polyols, such as graft polyols.

It is not necessary to remove the catalysts of the present invention after formation of the polyols prior to their utilization in polyurethane systems. In some embodiments it can be desirable, however, to remove the aluminum phosphonate catalysts prior to further utilization of the polyols. Any of the standard methods known in the art for removal of base catalysts or DMC catalysts can be utilized. One preferred method of removal of the aluminum phosphonate catalysts is through the use of binders for the aluminum such as magnesium silicate powders. One such example is Magnesol®, this compound includes acidic sites that bind the aluminum. The bound aluminum can then be filtered from the polyol prior to use of the polyols. Polyols of the invention may include amounts of aluminum phosphonate catalyst or residues thereof ranging from about 0.05 to about 5.0 weight percent of the final polyol based upon the amount of catalyst utilized and any processing of the polyol to remove the aluminum phosphonate catalyst.

One advantage of the aluminum phosphonate catalysts of the present invention is that because they are capable of producing polyols having such low unsaturation levels of, for example, less than 0.008 meq/g KOH, one can produce high functionality polyols. For example, it is possible using a triol initiator to produce a 6000 molecular weight triol having a 10 to 20 percent ethylene oxide cap with a functionality of 2.9. As would be understood by one of ordinary skill in the art, as the size of the polyol increases, the amount of unsaturation naturally increases, so what is considered very low unsaturation may be higher as the polyol size increases. What the present invention provides are polyols that have very low unsaturation when compared to the same size polyol made using base catalysts.

EXAMPLE 1

Oxypropylenation of a Diol Initiator Molecule

A 1 gallon nitrogen flushed autoclave is charged with 400 g of a polypropylene glycol having a number average molecular weight of 700 and 100 g of a 25% by weight solution of bis(diisobutylaluminum)methylphosphonate in toluene and tetrahydrofuran, with agitation. The solvent is removed by batch vacuum stripping at 110° C. for 0.5 hours. Then 1886 g of propylene oxide is fed into the autoclave at a rate of approximately 300 g/hour, at 110° C. and a pressure of less than 90 psig. The contents are reacted to constant pressure at 110° C. for approximately 5 hours. The autoclave is then evacuated to less than 10 mm Hg for 60 minutes. The vacuum is then relieved. The produced polyetherol is a clear fluid having a number average molecular weight of 4655, a hydroxyl number of 24.1 meq/g KOH and an unsaturation of 0.005 meq/g KOH.

EXAMPLE 2

Oxypropylenation of a Triol Initiator Molecule

A 5 gallon nitrogen flushed autoclave is charged with 1900 g of a glycerin propylene oxide adduct oligomer having a number average molecular weight of 700 and 220 g of a 25% by weight solution of bis(di-sec-butoxyaluminum)phenylphosphonate in toluene and tetrahydrofuran, with agitation. The solvent is removed by batch vacuum stripping at 110° C. for 0.5 hours. Then 14100 g of propylene oxide is fed into the autoclave at a rate of approximately 1000 g/hour, at 110° C. and a pressure of less than 90 psig. The rate of propylene oxide addition is adjusted as needed to maintain the concentration of unreacted propylene oxide at or below 8%. The contents are reacted to constant pressure at 110° C. for approximately 5 hours. The autoclave is then evacuated to less than 10 mm Hg for 60 minutes. The vacuum is then relieved with nitrogen, the contents cooled to 105° C. and transferred to a standard filter mix tank for removal of the catalyst. The contents are treated with 500 g of Magnesol® and 120 g of water for 1 hour at 105° C. The treated contents are recycled through the filter element until the filtrate is haze free indicating full removal of the particulate Magnesol® with bound catalyst. These filtration procedures are well known in the art and can comprise use of systems as simple as Buchner funnels with medium weight filter paper designed to remove particles in the size range of greater than 50 to 100 microns. The filtrate was then heated to 105° C. and vacuum stripped at less than 10 mm Hg for 1 hour. After 1 hour the vacuum is relieved with nitrogen. The clear fluid polyetherol has a number average molecular weight of 5744, a hydroxyl number of 29.3 meq/g KOH and an unsaturation of 0.008 meq/g KOH.

EXAMPLE 3

Oxyalkylenation of a Triol Initiator Molecule

A 5 gallon nitrogen flushed autoclave is charged with 3528 g of a glycerin propylene oxide adduct oligomer having a number average molecular weight of 700 and 250 g of a 25% by weight solution of bis(diisobutylaluminum) methylphosphonate in toluene and tetrahydrofuran, with agitation. The solvent is removed by batch vacuum stripping at 110° C. for 0.5 hours. Then a mixture of 8304 g of propylene oxide and 2010 g of ethylene oxide is fed into the autoclave at a rate of approximately 1 000 g/hour, at 110° C. and a pressure of less than 90 psig. The contents are reacted to constant pressure at 110° C. for approximately 3 hours. The autoclave is then vented to 34 psig and 1780 g of propylene oxide is fed at a rate of 2000 g/hour into the autoclave at 110° C. and a pressure of less than 90 psig. The contents are reacted to constant pressure at 110° C. for no more than 5 hours. The autoclave is then evacuated to less than 10 mm Hg for 60 minutes. Then the vacuum is relieved with nitrogen and the polyol recovered. The clear fluid polyetherol has a number average molecular weight of 2100, a hydroxyl number of 69.8 meq/g KOH and an unsaturation of 0.019 meq/g KOH.

EXAMPLE 4

Oxyalkylenation of a Triol Initiator Molecule

A 1 gallon nitrogen flushed autoclave is charged with 700 g of a glycerin propylene oxide adduct oligomer having a number average molecular weight of 700 and 100 g of a 25% by weight solution of bis(diisobutylaluminum) phenylphosphonate in toluene and tetrahydrofuran, with agitation. The solvent is removed by batch vacuum stripping at 110° C. for 0.5 hours. Then 2020 g of propylene oxide is fed into the autoclave at a rate of approximately 1000 g/hour, at 110° C. and a pressure of less than 90 psig. The contents are reacted to constant pressure at 110° C. for approximately 3 hours. The autoclave is then vented to 34 psig and 415 g of ethylene oxide is fed at a rate of 400 g/hour at 110° C. and a pressure of less than 90 psig. The contents are reacted to constant pressure at 110° C. for approximately 3 hours. The autoclave is then evacuated to less than 10 mm Hg for 60 minutes. Then the vacuum is relieved with nitrogen and the polyol recovered. The clear fluid polyetherol has a number average molecular weight of 3255, a hydroxyl number of 51.7 meq/g KOH and an unsaturation of 0.011 meq/g KOH.

EXAMPLE 5

Terminal Capping with Ethylene Oxide of a Triol Oligomer

A 1 gallon nitrogen flushed autoclave is charged with 2000 g of a glycerin propylene oxide adduct oligomer having a number average molecular weight of 3200 and 25 g of an approximately 40% by weight solution of bis(di-sec-butoxyaluminum)phenylphosphonate in toluene and tetrahydrofuran, with agitation. The solvent is removed by batch vacuum stripping at 125° C. for 0.5 hours. Then 360 g of ethylene oxide is fed into the autoclave at a rate of approximately 600 g/hour, at 130° C. and a pressure of less than 90 psig. The contents are reacted to constant pressure at 130° C. for approximately 1 hour. The autoclave is then evacuated to less than 10 mm Hg for 60 minutes. Then the contents are cooled to 80° C., the vacuum is relieved with nitrogen and the polyol is recovered. The clear fluid polyetherol has a number average molecular weight of 4906 and a hydroxyl number of 34.3 meq/g KOH, indicating addition of approximately 38 ethylene oxides per oligomer.

EXAMPLE 6

Comparison of KOH Catalyzed Polyols with Aluminum Phosphonate Catalyzed Polyols

A series of different sized polyols are prepared using a triol initiator and KOH catalyst. Using the same initiator a similar sized series of polyols are prepared according to Example 2. The results are presented in Table 1 below.

TABLE 1

| Catalyst used to form polyol | Number average molecular weight | Hydroxyl number, meq/g KOH | Unsaturation, meq/g KOH | Actual functionality |
| --- | --- | --- | --- | --- |
| KOH | 3,366 | 50.0 | 0.028 | 2.81 |
| KOH | 4,808 | 35.0 | 0.050 | 2.57 |
| KOH | 6,327 | 26.6 | 0.090 | 2.17 |
| Aluminum phosphonate | 2,805 | 60.0 | 0.007 | 2.96 |
| Aluminum phosphonate | 5,884 | 28.6 | 0.007 | 2.92 |
| Aluminum phosphonate | 6,983 | 24.1 | 0.005 | 2.94 |

The results demonstrate the extraordinary value of the present catalysts. The polyols produced using the aluminum phosphonate catalysts have a much higher functionality and much lower unsaturation level for a similar size polyol. The aluminum phosphonate catalysts can be used to provide terminal capping of polyols with an alkylene oxide. The suitable alkylene oxides include ethylene oxide, propylene oxide, butylene oxide and epichlorohydrin among others. When capping with the ethylene oxide the amount of terminal cap preferably ranges from 5 to 80% by weight based on the total weight of the polyetherol, and more preferably 5 to 20% by weight. When capping with propylene oxide the amount of terminal cap preferably ranges from 5 to 80% by weight based on the total weight of the polyetherol, and more preferably 5 to 15% by weight.

EXAMPLE 7

Comparative Formation of Foams

The procedure of Example 2 is used to form a triol polyol based on an initiator mixture of glycerin and a small amount of dipropylene glycol according to the procedure of the present invention, the triol is designated polyol A. Polyol A has a number average molecular weight of 2486, a hydroxyl number of 60.4 meq/g KOH, and an unsaturation of 0.011 meq/g KOH. The aluminum phosphonate catalyst is not removed from polyol A. Using the same initiator mixture a similar sized polyol, designated polyol B, is formed according to conventional procedures using KOH as the catalyst. The produced polyol has a number average molecular weight of 2600, a hydroxyl number of 57.6 meq/g KOH, and an unsaturation of 0.032 meq/g KOH. The KOH catalyst is removed from polyol B. Each polyol is then used to form a polyurethane foam. The foams are prepared using conventional procedures and the components listed in Table 2 below. The amount of tin catalyst is slightly increased in Foam A because of the acidity of the residual phosphonate.

TABLE 2

| Component | Foam A, amount in grams | Foam B, amount in grams |
| --- | --- | --- |
| Polyol A | 400.00 | 0.00 |
| Polyol B | 0.00 | 400.00 |
| Dabco ® 33-LV amine | 0.25 | 0.25 |
| BF-2370 surfactant | 1.00 | 1.00 |
| Water | 4.00 | 4.00 |
| T-10 tin catalyst | 0.60 | 0.45 |
| Toluene diisocyanate | 212.20 | 210.30 |

The foams A and B were then tested for airflow, hardness, tear, elongation, and compression set. The results are presented below in Table 3. All parameters were tested according to ASTM method D 3574 except for the compression set wet method. The compression set wet method used is the same as JIS K-6400, Japanese Industry Standards. The method will be included as test L of ASTM method D 3574 in 2002. Briefly, the method is exposure at 50° C., 95% relative humidity for 22 hours followed by a 30-minute recovery period.

TABLE 3

| Foam | Air flow, Cubic feet/ minute | Hardness, lbs./foot | Tear, PPI | Break Elongation, heat aged, % | Compression set wet, % |
| --- | --- | --- | --- | --- | --- |
| Foam A | 4.67 | 70.48 | 1.60 | 136.62 | 3.41 |
| Foam B | 3.88 | 74.64 | 1.75 | 129.34 | 3.09 |

The results demonstrate that foam A produced using polyol A, prepared according to the present invention, has very similar to even better properties when compared to foam B prepared from polyol B, a KOH catalyzed polyol. Furthermore polyol A, produced according to the present invention, has the additional advantages of a much lower unsaturation and no need to remove the catalyst prior to preparation of the foam.

The foregoing invention has been described in accordance with the relevant legal standards, thus the description is exemplary rather than limiting in nature. Variations and modifications to the disclosed embodiment may become apparent to those skilled in the art and do come within the scope of the invention. Accordingly, the scope of legal protection afforded this invention can only be determined by studying the following claims.

What is claimed is:

1. A polyether polyol formed according to a process comprising the steps of:
   a) providing at least one alkylene oxide;
   b) providing at least one initiator molecule having at least one alkylene oxide reactive hydrogen; and
   c) reacting the at least one alkylene oxide with the at least one initiator molecule in the presence of an aluminum phosphonate catalyst to form a polyether polyol comprising the aluminum phosphonate catalyst or residue thereof.

2. The polyether polyol of claim 1, wherein step a) comprises providing ethylene oxide, propylene oxide, butylene oxide, epichlorohydrin or mixtures of these alkylene oxides.

3. The polyether polyol of claim 1, wherein step b) comprises providing as the at least one initiator molecule, an alcohol, a polyhydroxyl compound, a mixed hydroxyl and amine compound, a polyamine compound, or mixtures of these initiator molecules.

4. The polyether polyol of claim 1, wherein
   a) step b) comprises providing as the at least one initiator molecule, an oligomer comprising the reaction product of a pre-reaction initiator molecule with at least one alkylene oxide and
   b) step c) comprises using the oligomer as the initiator molecule.

5. The polyether polyol of claim 4, wherein said oligomer has a number average molecular weight of from 200 to 1500 Daltons.

6. The polyether polyol of claim 1, wherein step c) comprises providing the aluminum phosphonate catalyst in an amount of from 0.1 to 5.0 weight percent based on the total weight of the polyether polyol.

7. The polyether polyol of claim 1, wherein step c) comprises providing as the aluminum phosphonate catalyst an aluminum phosphonate having the general structure of RPO-(OAlR'R")$_2$ wherein: 0 represents oxygen; P represents pentavalent phosphorous; Al represents aluminum; R comprises a hydrogen, an alkyl ground, or an aryl group; and R' and R' independently comprise a halide, an alkyl group, an alkoxy group, an aryl group, or an aryloxy group.

8. The polyether polyol of claim 7, comprising providing as the aluminum phosphonate catalyst an aluminum phosphonate wherein: R is a methyl group; and R' and R" independently comprise one of an ethyl group, an ethoxy group, a propyl group, a propoxy group, a butyl group, a butoxy group, a phenyl group, or a phenoxy group.

9. The polyether polyol of claim 1, wherein step c) comprises reacting the at least one alkylene oxide with the at least one initiator molecule in the presence of the aluminum phosphonate catalyst to form a polyether polyol having an unsaturation of less than or equal to 0.020 meq/g KOH.

10. The polyether polyol of claim 1, wherein step c) comprises reacting the at least one alkylene oxide with the at least one initiator molecule in the presence of the aluminum phosphonate catalyst to form a polyether polyol having an unsaturation of less than or equal to 0.015 meq/g KOH.

11. A polyether polyol formed according to a process comprising the steps of:
   a) providing at least one alkylene oxide;
   b) providing at least one initiator molecule having at least two alkylene oxide reactive hydrogens;
   c) providing an aluminum phosphonate catalyst having the general structure of RPO-(OAlR'R")2 wherein: 0 represents oxygen; P represents pentavalent phosphorous; Al represents aluminum; R comprises a hydrogen, an alkyl group, or an aryl group; and R' and R" independently comprise a halide, an alkyl group, an alkoxy group, an aryl group, or an aryloxy group; and d) reacting the at least one alkylene oxide with the at least one initiator molecule in the presence of the aluminum phosphonate catalyst to form a polyether polyol comprising the aluminum phosphonate catalyst or residue thereof.

12. The polyether polyol of claim 11, wherein step a) further comprises providing ethylene oxide, propylene oxide, butylene oxide, epichlorohydrin or mixtures of these alkylene oxides.

13. The polyether polyol of claim 11, wherein step b) comprises providing as the at least one initiator molecule a polyhydroxyl compound, a mixed hydroxyl and amine compound, a polyamine compound, or mixtures of these initiator molecules.

14. The polyether polyol of claim 11, wherein
a) step b) comprises providing as the at least one initiator molecule, an oligomer comprising the reaction product of a pre-reaction initiator molecule with at least one alkylene oxide and
b) step c) comprises using the oligomer as the initiator molecule.

15. The polyether polyol of claim 14, wherein said oligomer has a number average molecular weight of from 200 to 1500 Daltons.

16. The polyether polyol of claim 11, wherein step c) comprises providing the aluminum phosphonate catalyst in an amount of from 0.1 to 5.0 weight percent based on the total weight of the polyether polyol.

17. The polyether polyol of claim 11, wherein step c) comprises providing as the aluminum phosphonate catalyst an aluminum phosphonate wherein:

R is a methyl group;

and R' and R' independently comprise one of an ethyl group, an ethoxy group, a propyl group, a propoxy group, a butyl group, a butoxy group, a phenyl group, or a phenoxy group.

18. The polyether polyol of claim 11, having an unsaturation of less than or equal to 0.020 meq/g KOH.

19. The polyether polyol of claim 11, having an unsaturation of less than or equal to 0.015 meq/g KOH.

20. A polyether polyol formed according to a process comprising the steps of:

a) providing propylene oxide;
b) providing at least one initiator molecule having at least one propylene oxide reactive hydrogen; and
c) reacting the propylene oxide with the at least one initiator molecule in the presence of an aluminum phosphonate catalyst to form a polyether polyol comprising the aluminum phosphonate catalyst or residue thereof.

21. The polyether polyol of claim 20 comprising the further step of reacting the polyether polyol formed in step c) with ethylene oxide in the presence of an aluminum phosphonate catalyst to thereby form terminal caps of ethylene oxide.

22. The polyether polyol of claim 21 comprising terminal caps of ethylene oxide in an amount of from 5 to 80% by weight based on the total weight of the polyether polyol.

23. The polyether polyol of claim 20 wherein step b) comprises providing at least one diol initiator molecule having at least two propylene oxide reactive hydrogens.

24. A heteric polyether polyol formed according to a process comprising the steps of:

a) providing a mixture of alkylene oxides;
b) providing at least one initiator molecule having at least one alkylene oxide reactive hydrogen; and
c) reacting the mixture of alkylene oxides with the at least one initiator molecule in the presence of an aluminum phosphonate catalyst to form a heteric polyether polyol comprising the aluminum phosphonate catalyst or residue thereof.

25. The heteric polyether polyol of claim 24 comprising the further step of reacting the heteric polyether polyol formed in step c) with ethylene oxide or propylene oxide in the presence of an aluminum phosphonate catalyst to thereby form terminal caps.

26. The heteric polyether polyol of claim 25 wherein said terminal caps comprise ethylene oxide in an amount of from 5 to 20% by weight of the total weight the polyether polyol.

27. The heteric polyether polyol of claim 25 wherein said terminal caps comprise propylene oxide in an amount of from 5 to 15% by weight of the total weight of the polyether polyol.

28. A polyether polyol formed according to a process comprising the steps of:

a) providing ethylene oxide;
b) providing at least one initiator molecule having at least one ethylene oxide reactive hydrogen; and
c) reacting the ethylene oxide with the at least one initiator molecule in the presence of an aluminum phosphonate catalyst to form a polyether polyol comprising the aluminum phosphonate catalyst or residue thereof.

29. The polyether polyol of claim 28 comprising the further step of reacting the polyether polyol formed in step c) with propylene oxide in the presence of an aluminum phosphonate catalyst to thereby form terminal caps of propylene oxide.

30. The polyether polyol of claim 29 wherein said terminal caps of propylene oxide comprise from 5 to 80% by weight of the total weight of the polyether polyol.

31. A polyether polyol formed according to a process comprising the steps of:

a) providing at least one alkylene oxide;
b) providing at least one oligomer having at least one alkylene oxide reactive hydrogen; and
c) reacting the alkylene oxide with the at least one oligomer in the presence of an aluminum phosphonate catalyst to form a polyether polyol comprising the aluminum phosphonate catalyst or residue thereof.

32. The polyether polyol of claim 31 wherein said at least one oligomer has a number average molecular weight of from 200 to 1500 Daltons.

33. A linear block copolymer polyether polyol formed according to a process comprising the steps of:

a) providing a first alkylene oxide;
b) providing at least one diol initiator molecule having two alkylene oxide reactive hydrogens; and
c) reacting the first alkylene oxide with the at least one diol initiator molecule in the presence of an aluminum phosphonate catalyst to form a linear polyether polyol; and
d) reacting the reaction product of step c) with a second alkylene oxide other than the first alkylene oxide in the presence of the aluminum phosphonate catalyst to form a linear block copolymer polyether polyol comprising the aluminum phosphonate catalyst or residue thereof.

34. The polyether polyol of claim 33, wherein the first alkylene oxide and the second alkylene oxide are selected from the group consisting of ethylene oxide, propylene oxide, butylene oxide, epichlorohydrin and mixtures thereof such that the first alkylene oxide is different from the second alkylene oxide.

35. A composition of matter comprising:
a) a polyether polyol; and
b) an aluminum phosphonate having the general structure of RPO-(OAlR'R")2 wherein:

P represents pentavalent phosphorous;

R comprises a hydrogen, an alkyl group, or an aryl group; and

R' and R" independently comprise a halide, an alkyl group, an alkoxy group, an aryl group, or an aryloxy group.

36. The composition of matter as recited in claim 35 wherein:

R is a methyl group; and

R' and R" independently comprise one of an ethyl group, an ethoxy group, a propyl group, a propoxy group, a butyl group, a butoxy group, a phenyl group, or a phenoxy group.

37. The composition of matter as recited in claim 35 wherein said aluminum phosphonate is present at levels of from approximately 0.01 to 5.0 weight percent based on the total weight of the polyether polyol.

38. The polyether polyol of claim 1 having a number average molecular weight of from 1,500 to 10,000 Daltons.

39. The polyether polyol of claim 1 comprising an amount of from 0.05 to 5.0 weight percent of the aluminum phosphonate catalyst or residue thereof, based on the total weight of the polyether polyol.

40. The polyether polyol of claim 14 having a number average molecular weight of from 1,500 to 10,000 Daltons.

41. The polyether polyol of claim 11 comprising an amount of from 0.05 to 5.0 weight percent of the aluminum phosphonate catalyst or residue thereof, based on the total weight of the polyether polyol.

42. The polyether polyol of claim 20 having a number average molecular weight of from 1,500 to 10,000 Daltons.

43. The polyether polyol of claim 20 having an unsaturation of less than or equal to 0.015 meq/g KOH.

44. The polyether polyol of claim 20 comprising an amount of from 0.05 to 5.0 weight percent of the aluminum phosphonate catalyst or residue thereof, based on the total weight of the polyether polyol.

45. The heteric polyether polyol of claim 24 having a number average molecular weight of from 1,500 to 10,000 Daltons.

46. The heteric polyether polyol of claim 24 an unsaturation of less than or equal to 0.0 15 meq/g KOH.

47. The heteric polyether polyol of claim 24 comprising an amount of from 0.05 to 5.0 weight percent of the aluminum phosphonate catalyst or residue thereof, based on the total weight of the heteric polyether polyol.

48. The polyether polyol of claim 28 having a number average molecular weight of from 1,500 to 10,000 Daltons.

49. The polyether polyol of claim 28 an unsaturation of less than or equal to 0.015 meq/g KOH.

50. The polyether polyol of claim 28 comprising an amount of from 0.05 to 5.0 weight percent of the aluminum phosphonate catalyst or residue thereof, based on the total weight of the polyether polyol.

51. The polyether polyol of claim 31 having a number average molecular weight of from 1,500 to 10,000 Daltons.

52. The polyether polyol of claim 31 an unsaturation of less than or equal to 0.015 meq/g KOH.

53. The polyether polyol of claim 31 comprising an amount of from 0.05 to 5.0 weight percent of the aluminum phosphonate catalyst or residue thereof, based on the total weight of the polyether polyol.

54. The polyether polyol of claim 33 having a number average molecular weight of from 1,500 to 10,000 Daltons.

55. The polyether polyol of claim 33 an unsaturation of less than or equal to 0.015 meq/g KOH.

56. The polyether polyol of claim 33 comprising an amount of from 0.05 to 5.0 weight percent of the aluminum phosphonate catalyst or residue thereof, based on the total weight of the polyether polyol.

57. The composition of matter as recited in claim 35 wherein the polyether polyol has a number average molecular weight of from 1,500 to 10,000 Daltons.

58. The composition of matter as recited in claim 35 wherein the polyether polyol has an unsaturation of less than or equal to 0.015 meq/g KOH.

59. The composition of matter as recited in claim 35 the polyether polyol comprises an amount of from 0.05 to 5.0 weight percent of the aluminum phosphonate catalyst or residue thereof, based on the total weight of the polyether polyol.

* * * * *